United States Patent [19]
Siwruk et al.

[11] Patent Number: 5,516,891
[45] Date of Patent: May 14, 1996

[54] LIQUID PHASE SYNTHESIS OF PEPTIDES AND PEPTIDE DERIVATIVES

[75] Inventors: Gary A. Siwruk, Franklin; John S. Eynon, Bellingham, both of Mass.

[73] Assignee: Kinerton, Ltd., Ireland

[21] Appl. No.: 190,111

[22] PCT Filed: Jun. 16, 1993

[86] PCT No.: PCT/US93/05783

§ 371 Date: May 25, 1994

§ 102(e) Date: May 25, 1994

[87] PCT Pub. No.: WO93/25571

PCT Pub. Date: Dec. 23, 1993

[30] Foreign Application Priority Data

Jun. 16, 1992 [IE] Ireland ................................. 921942

[51] Int. Cl.$^6$ ............................. C07K 1/02; C07K 1/10; C07K 5/103
[52] U.S. Cl. ............................................ 530/330; 530/341
[58] Field of Search .................................. 530/330, 338, 530/339, 340, 341

[56] References Cited

U.S. PATENT DOCUMENTS

| | | | |
|---|---|---|---|
| 3,121,707 | 2/1964 | Anderson et al. | 530/341 |
| 3,769,271 | 10/1973 | Southard | 530/327 |
| 4,250,086 | 2/1981 | Heavner | 530/341 |
| 4,407,794 | 10/1983 | Roques et al. | 514/18 |
| 4,581,168 | 4/1986 | Diaz et al. | 530/324 |
| 4,658,016 | 4/1987 | Konig et al. | 530/339 |
| 4,755,591 | 7/1988 | Konig et al. | 530/338 |
| 5,004,781 | 4/1991 | Rink | 530/333 |
| 5,202,418 | 4/1993 | Lebl et al. | 530/334 |

FOREIGN PATENT DOCUMENTS

| | | | |
|---|---|---|---|
| 289762 | 11/1989 | Germany | C07C 213/02 |
| WO88/00594 | 1/1988 | WIPO | C07K 1/100 |

OTHER PUBLICATIONS

Carpino et al., "The 9–Fluorenylmethoxycarbonyl Amino––Protecting Group", J. Org. Chem., 37:3404–3409, 1972.
Wang et al., "One–Pot Liquid–Phase Synthesis of DSIP and 5–Phe–DSIP Using Fluoren-9-yl-methoxycarbonyl–Protected Amino Acid Pentafluorophenyl Esters", Synthesis, 9:845–846, 1990.
Gross et al, The Peptides: Analysis, Synthesis, Biology, published 1981 by Academic Press (New York), pp. 22–24, 225.
Jensen, et al., "A New Method for Rapid Solution Synthesis of Shorter Peptides by use of PyBOP", Tetrahedron Letters, vol. 32, No. 44, pp. 6387–6390, 1991.
Lenfant, et al., "Enhancement of the Adherence of Hematopoietic Stem Cells to Mouse Bone Marrow–derived Stromal Cell Line MS–1–T by a Tetrapeptide Acetyl–N–Ser–Asp–Lys–Pro", Exp. Hematol. 17:898–902, 1989.
E. Atherton et al., "The Peptides", vol. 9, pp. 32–39, 1987.
Gregg B. Fields et al., "Solid phase peptide synthesis utilizing 9–fluorenylmethoxycarbonyl amino acids", Aug. 23, 1989, Int. J. Peptide Res. 35, pp. 161, 181–183, 186, 187.
Derek Hudson, "Methodological Implications of Simultaneous Solid–Phase Peptide Synthesis. 1. Comparison of Different Coupling Procedures", American Chemical Society, 1988, pp. 618–623.
Thierry et al., "Synthesis and Activity of NAcSerAspLysPro Analogues on Cellular Interactions between T–Cell and Erythrocytes in Rosette Formation", American Chemical Society, 1990, pp. 2123–2127.

Primary Examiner—Jeffrey E. Russel
Attorney, Agent, or Firm—Fish & Richardson; William E. McGowan

[57] ABSTRACT

A liquid phase peptide synthetic method which uses (1) Fmoc as the protecting group for the non-side chain amino functionality, (2) ammonia, a primary or secondary amine to remove the Fmoc protecting group, and (3) substituted carbodiimide as the coupling agent for the C to N synthesis of peptides or peptide derivatives in a proper organic solvent.

38 Claims, 4 Drawing Sheets

START

LIQUID PHASE SYNTHESIS OF PEPTIDES AND PEPTIDE DERIVATIVES

BACKGROUND OF THE INVENTION

Classical liquid phase peptide synthesis involves the well-known problems of many manipulations and considerable loss of material during the isolation and purification of intermediates.

Some of these problems have been circumvented by using continuous liquid phase techniques. Furthermore, numerous advances made in solid phase peptide synthesis have led to progress in liquid phase synthetic methods. For example, the protecting groups developed in solid phase synthesis are also useful in liquid phase synthesis.

The two major routes in liquid phase synthesis are (1) use of the t-butyloxycarbonyl protecting group ("Boc") to block the non-side chain amino functionality, and (2) use of the 9-fluoroenyl methoxycarbonyl protecting group ("Fmoc") to block the same functionality. For examples, see Thierry, J. et al. J. Med. Chem. 33:2122 (1990) and Høeg-Jensen, T. et al. Tetrahedron Letters 32:6387 (1991).

No continuous liquid phase peptide synthetic methods using Fmoc as the protecting group and a substituted carbodiimide as the coupling agent have hitherto been reported.

SUMMARY OF THE INVENTION

The present invention relates to a continuous liquid phase synthetic method for preparing a peptide containing 2–10 amino acid residues with or without modification at the C-terminus or an N-acyl derivative thereof, which method comprises the steps of:

(a) coupling a first amino acid or a derivative thereof to a second amino acid via an amide bond in an organic solvent containing a substituted carbodiimide, with the first amino acid or derivative thereof having both its non-side chain carboxyl functionality and its side-chain functionalities, if any and necessary, blocked by base-stable groups and a second amino acid with its non-side chain amino functionality blocked by Fmoc and its side chain functionalities, if any and necessary, blocked by base-stable groups;

(b) detaching the Fmoc with ammonia, a primary amine, or a secondary amine;

(c) coupling an additional amino acid to the Fmoc-detached coupled product via an amide bond in an organic solvent containing a substituted carbodiimide, with the additional amino acid having its non-side chain amino functionality blocked by Fmoc and its side chain functionalities, if any and necessary, blocked by basestable groups;

(d) detaching the Fmoc with ammonia, a primary amine, or a secondary amine;

(e) repeating steps (c) and (d) until the length of the peptide or the N-acyl derivative is achieved;

(f) acylating the non-side chain amino group of the Fmoc-detached coupled product from the previous step; and (g) detaching the base-stable groups;

In the above-described method, the first amino acid or derivative thereof corresponds to a first residue (i.e., the C-terminal residue) in the peptide or its N-acyl derivative, the second amino acid corresponds to a second residue adjacent to the first residue in the peptide or its N-acyl derivative, and the additional amino acid corresponds to a third residue adjacent to the second residue in the peptide or its N-acyl derivative. (In other word, consecutive amide coupling is performed in the C terminus to N terminus direction with one amino acid linked to another based on the sequence of the peptide or its N-acyl derivative to be synthesized.) Furthermore, when the peptide or the N-acyl derivative contains two amino acid residues, steps (c) through (e) are omitted. In addition, when the peptide, rather than the N-acyl derivative, is to be synthesized, step (f) is omitted.

Note that the carboxyl and amino groups which participate in the formation of an amide bond are called non-side chain functionalities. On the other hand, any functional groups which are not involved in formation of such a bond are called side chain functionalities.

A peptide without modification at the C-terminus refers to a peptide with a carboxylic group at its C-terminus (i.e., $\alpha$-COOH of the C-terminal residue in most naturally-occurring peptides). A peptide with modification at the C-terminus, on the other hand, refers to a peptide, which, instead of having a carboxylic group at its C-terminus as described above, possesses a C-terminal amide or substituted amide (i.e., $CONH_2$ or $CONHR$, where R is alkyl, arylalkyl or aryl), a C-terminal ester (i.e., $COOR$, where R is alkyl, arylalkyl or aryl), or a C-terminal alcohol (i.e., $CH_2OH$).

What is meant by "an N-acyl derivative of a peptide" is a peptide with a hydrogen of its non-side chain amino functionality at the N-terminus replaced by an acyl chain containing 1 to 12 carbons, inclusive (e.g., formyl, acetyl, benzoyl, hexanoyl, or naphthoyl).

What is meant by "an amino acid or derivative thereof" is an amino acid or its derivative. An amino acid derivative refers to an amino acid the carboxylic group of which (i.e., $\alpha$-carboxyl in an $\alpha$-amino acid derivative) has been replaced by an amide or a substituted amide, an ester, or an alcohol, as defined above; i.e., see the definition of a C-terminal amide or substituted amide, a C-terminal ester, or a C-terminal alcohol in a peptide with modification at its C-terminus.

Preferably, in the present synthetic method, the organic solvent used is methylene chloride, chloroform, dichloroethane, dimethylformamide, dimethylacetamide, tetrahydrofuran, ethyl acetate, acetonitrile, or a combination of the above solvents; the substituted carbodiimide is diisopropylcarbodiimide, dicyclohexylcarbodiimide, or N-ethyl-N'-(3-dimethylaminopropyl)carbodiimide; the Fmoc is detached with 4-(aminomethyl)piperidine, piperidine, or tris (2-aminoethyl) amine; the detached Fmoc is removed by filtration and subsequent washing with an acidic aqueous solution, e.g., a phosphate buffer, pH 5.5.

In a particular preferred embodiment, the organic solvent is methylene chloride and the Fmoc is detached with 4-aminomethylpiperidine.

It is also preferred that the base-stable groups be detached with trifluoroacetic acid in the synthetic method of this invention.

Further, where the N-acyl derivative is to be synthesized, it is preferable that a strong base, such as triethylamine or diisopropylethylamine, be added in step (f).

Note that the term "base-stable group" refers to protecting groups used to obstruct functionalities of the amino acid building blocks which (1) are base stable, i.e., cannot be removed by bases, such as 4-aminomethylpiperidine, piperidine, or tris (2-aminoethyl) amine, which are used to remove Fmoc, and (2) can be removed by an acid, such as trifluoroacetic acid, or by other means, such as catalytic hydrogenation. The symbol "Fmoc" is used herein and in the appended claims to stand for the 9-fluoroenyl methoxycarbonyl group.

The above-described synthetic method can be used to prepare a tetrapeptide (e.g., H-Ser-Asp-Lys-Pro-OH (SEQ ID NO:1)) or an N-acyl derivative of a tetrapeptide (e.g., Acetyl-Ser-Asp-Lys-Pro-OH (SEQ ID NO:2)). When H-Ser-Asp-Lys-Pro-OH (SEQ ID NO:1) or Acetyl-Ser-Asp-Lys-Pro-OH (SEQ ID NO:2) is to be synthesized, the base-stable protecting groups used to block the side chain functionalities of Ser, Asp, Lys and Pro can be t-butyl, t-butyl, t-butyl- oxycarbonyl, and t-butyl, respectively.

In the formula H-Ser-Asp-Lys-Pro-OH (SEQ ID NO:1), each of the conventional three-letter amino acid symbols (e.g., Ser) represents a structural residue. For example, the symbol Ser in the above formula stands for -NH-CH(CH$_2$OH)-CO-. The formula Acetyl-Ser-Asp-Lys-Pro-OH (SEQ ID NO:2) stands for an N-acyl peptide derivative whose amino functionality (i.e., $\alpha$-amino of Ser) is substituted with an acetyl group.

The above-described method is advantaged in that it uses substituted carbodiimides, which are rather inexpensive, as the coupling agent and is thus most suitable for large-scale continuous liquid phase peptide synthesis. Other features and advantages of the invention will be apparent from the following detailed description, and from the claims.

BRIEF DESCRIPTION OF THE DRAWINGS

The drawings will first be briefly described.

DESCRIPTION OF THE PREFERRED EMBODIMENTS

Figure 1A:
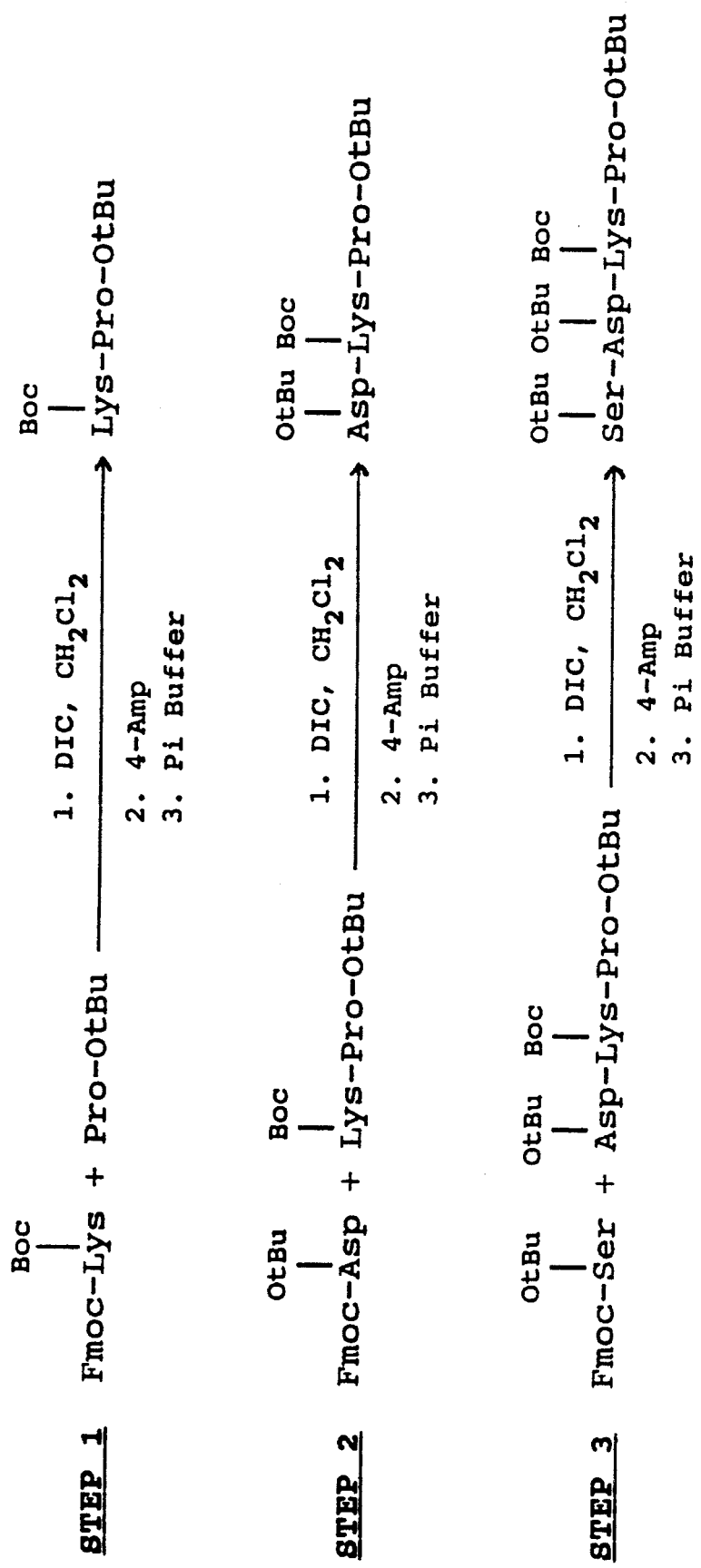
FIG. 1 is a scheme for synthesizing Acetyl-Ser-Asp-Lys-Pro-OH (SEQ ID NO:2) following a preferred method of the present invention.

The present invention is an improvement of the conventional liquid phase peptide synthetic method. In particular, it teaches the use of Fmoc as the protecting group for the non-side chain amino functionality, the use of ammonia, a primary or secondary amine [e.g., 4-aminomethyl-piperidine, piperidine, or tris (2-aminoethyl) amine] to remove the Fmoc protecting group, and the use of a selected substituted carbodiimide [e.g., diisopropylcarbodiimide, dicyclohexylcarbodiimide, or N-ethyl-N' -(3-dimethyl-aminopropyl)carbodiimide] as the coupling agent for the C terminus to N terminus synthesis of peptides in a proper organic solvent. Proper solvents include, but are not limited to, methylene chloride, chloroform, dichloroethane, dimethylformamide, and combination thereof; minor modification of the procedures might be necessary in using different solvents.

The above teachings enable one to use washes with an acidic aqueous solution for removal of excess reagents or undesired products thereof. For example, when 4-aminomethylpiperidine is used to remove Fmoc, any excess 4-aminomethylpiperidine, 9-(4'-aminomethylpiperidinylmethyl) fluorene (i.e., a 4-aminomethylpiperidine/Fmoc product), and the product from amino acid coupled to 4-aminomethylpiperidine can be extracted by a phosphate buffer, pH 5.5.

Furthermore, trace amounts of the coupling agent and its product can also be readily removed by the phosphate buffer.

According to the present invention, the byproducts and excess reagents can also be removed by filtration. For instance, when diisopropylcarbodiimide is used as the coupling agent, diisopropyl urea formed from it is partially soluble in methylene chloride, thus enabling one to remove the insoluble amount by filtration (e.g., vacuum filtration). The product from the reaction of 4-aminomethylpiperidine and the Fmoc group is also partially soluble in methylene chloride and some of it can likewise be removed by filtration. Such partial removal is preferred, since it reduces the chance of an emulsion forming upon addition of an aqueous solution for further extraction of excess reagents. Cooling is desired before filtration, since it generally further reduces the solubility of the partially soluble materials, and lowers the vapor pressure of the organic solvent, thus facilitating the subsequent vacuum filtration.

The above-described techniques, i.e., aqueous extraction and filtration to remove excess reagents and undesired products, are rather simple. Employment thereof enables one to eliminate the tedious and time-consuming steps of purifying intermediates chromatographically; such steps are used in the conventional liquid phase peptide synthesis. As a result, the cycle time can be greatly reduced to one or two hours, permitting several cycles to run per day.

As mentioned above, the Fmoc protecting group can be removed by use of bases such as ammonia, a primary amine or a secondary amine. (Note that Fmoc is stable to tertiary amines, such as triethylamine and diisopropylethylamine.) An advantage of using the base labile Fmoc group is that it eliminates the neutralization step of the deprotected non-side chain amino group, as is required when the t-butyloxycarbonyl ("Boc") protecting group is used. Thus, the addition of the next Fmoc-protected amino acid to the free amino group readily proceeds and the cycle can be repeated to build the peptide chain.

The side chain protecting groups used in the present invention, in contrast to Fmoc, must be stable to bases such as ammonia, a primary amine or a secondary amine, so that they remain intact under conditions when Fmoc is removed. Furthermore, after all protected amino acids have been linked together, the side chain protecting groups must also be readily removable by an acid, e.g., trifluoroacetic acid, or by catalytic hydrogenation, e.g., when benzyl is used as the protecting group.

A side chain amino functionality, such as $\epsilon$-amino of Lys, can be protected by Boc, carbobenzoxy, or 2-chloro-carbobenzoxy.

A side chain carboxyl functionality, such as $\beta$-carboxyl of Asp, can be protected by t-butyl (ester), benzyl (ester), or cyclohexyl (ester). The same protecting groups can also be used to block the non-side chain carboxyl functionality of the C-terminal amino acid.

A side chain hydroxyl functionality, such as that in Ser or Tyr, can be protected by t-butyl (ether) or benzyl (ether).

A side chain thiol functionality, such as that in Cys, can be protected by trityl (i.e., triphenylmethyl).

Other aspects of the present invention are well known in the art and will briefly discussed below.

Preparation of Peptides with Modification at the C-terminus

When a peptide with modification at the C-terminus is to be prepared, an amino acid derivative must be used in the first coupling reaction. The non-side chain functional group of the amino acid derivative can be subjected to the coupling reaction either with or without protection.

For example, when the C-terminal residue is an amide or a substituted amide, an amino acid derivative which is an amide or substituted amide can be introduced at the inception of the synthesis. This is because the amide or substituted amide functionalities are stable to the synthetic reagents.

As for peptides with a C-terminal ester, an amino ester which is acid and base stable (i.e., benzyl esters) can also be introduced at the inception of the synthesis, if catalytic hydrogenation conditions, which are used to cleave benzyl esters, are not used in any of the subsequent deprotecting steps. On the other hand, amino esters which are acid or base labile can be introduced at the inception of the synthesis only if they are stable to reagents used for the deprotection of the functionalities in the subsequent steps. Also, if an additional acidic functionality is present within the peptide sequence, the corresponding protection group should be orthogonal.

Amino alcohols are stable to the synthetic reagents and can be introduced at the inception of the synthesis of a peptide alcohol. An ether linkage can also be used to promote stability or solubility, if desired.

Scavengers

Scavengers react with the carbonium ions that can form when protecting groups are removed from the peptide. Amino acids containing aromatic rings are easily alkylated or acylated by carbonium ions. Thus, it is preferable that scavengers be used at the deprotecting step. The carbonium ions present in the cleavage reaction can react with a scavenger or scavengers.

The types of scavengers to be used depend on the amino acids in the peptide. The most common scavengers are anisole, indole, phenol, water, mercaptoethanol, ethanedithiol, thiophenol, and dithiothreitol.

Neutralization

When a hydrochloride salt of the C-terminal amino acid (with its side chain functionality, if any, and its non-side chain carboxyl group protected) of the peptide to be synthesized is used, a strong base, such as triethylamine or diisopropylethylamine, is first used to neutralize the non-side chain amino group before the coupling reaction. More specifically, the strong base forms a hydrochloride salt which is partially insoluble in the organic solvent used and can be removed by vacuum filtration and aqueous extraction.

Similarly, when N-acylated peptide is to be prepared, it is preferable that a strong base be used to react with any acid produced from the acylation reaction, thereby preventing salt formation between the amino group of the N-terminal amino acid with the acid.

Acylation

Acylation of the amino group of a peptide, either in the side chain or in the non-side chain, can be effected by an acid anhydride. For example, acetic anhydride $Ac_2O$ can be used for acetylation. Similarly, activated formic acid, such as mixed anhydrides (e.g., H-CO-O-CO-R, where R is H, $CH_3$ or $CF_3$) can be used for formylation. As another example, naphthoic acid or anhydride can be used to introduce a naphthoyl group to the N-terminus of a peptide.

The coupling and deblocking reactions can be readily monitored by thin layer chromatography ("T.L.C."). The purity of the crude peptide, on the other hand, can be checked by either T.L.C. or high pressure liquid chromatography ("H.P.L.C."). The crude peptide can be further purified by H.P.L.C. and lyophilized to give the peptide as a powder.

The continuous Fmoc solution method described above is a practical alternative to solid phase synthesis suitable for scale-up and is commercially attractive.

Without further elaboration, it is believed that a person of ordinary skill in the art can, using the preceding description, utilize the present invention to its fullest extent. The two specific working examples provided below are, therefore, to be construed as merely illustrative, and not limitative of the remainder of the disclosure in any way whatsoever. For example, while ∝-amino acids are the building blocks in both examples, β- or γ-amino acids can also be used to prepare other peptides or derivatives thereof in an analogous fashion. By the same token, although peptide/peptide derivative with a C-terminal carboxyl group were prepared in the working examples below, peptides with a C-terminal amide, ester or alcohol can be prepared in a similar manner with modifications well known in the art, e.g., see discussion above under the heading "Preparation of Peptides with Modification at the C-terminus".

Below are the two T.L.C. systems which were used in the following working examples for monitoring the coupling reaction and the reaction of removing the protecting Fmoc group:

T.L.C. System One: methylene chloride:acetone 9:2, UV/ninhydrin

T.L.C. System Two: n-butanol:acetic acid:water 4:1:1, UV/ninhydrin

EXAMPLE 1

Synthesis of Acetyl-Ser-Asp-Lys-Pro-OH (SEQ ID NO:2)

Figure 1B:
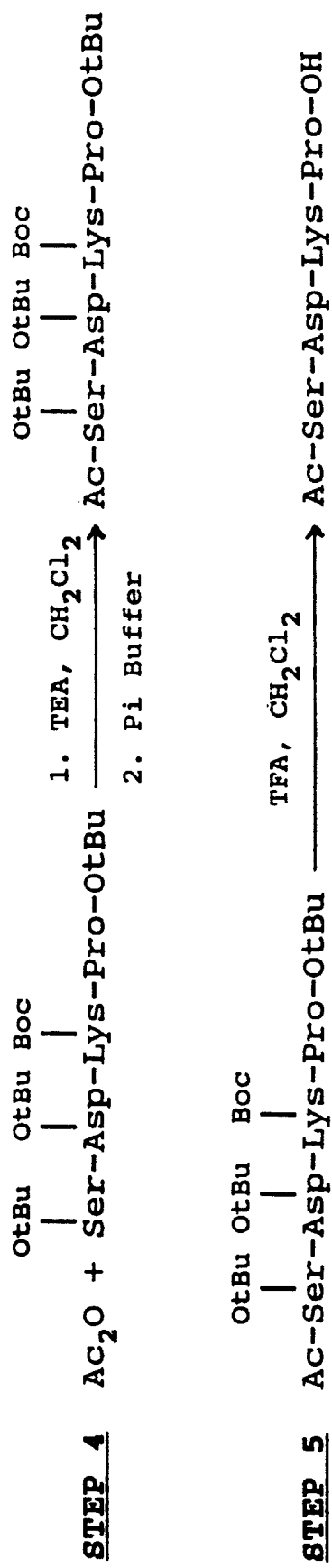

FIG. 1 shows the scheme followed to prepare Acetyl-Ser-Asp-Lys-Pro-OH.

A four liter Erlenmeyer flask equipped with magnetic stir bar was charged with 45.9 grams (0.221 moles) L-Proline-t-butyl ester. hydrochloride, 113.9 grams (0.243 moles) of Fmoc-(BOC-L-Lysine) and 1.2 liters of methylene chloride. The suspension was stirred and 30.7 grams (0.243 moles) of diisopropylcarbodiimide and 22.4 grams (0.221 moles) of triethylamine were added. In this step, the amino group of Proline-t-butyl esterhydrochloride was neutralized by the added triethylamine (not shown in FIG. 1). The mixture was stirred for 2 hours. T.L.C. (System One) indicated that the reaction was complete.

With the suspension being stirred, 441 mls (3.661 moles) of 4-aminomethylpiperidine was added and stirred for one hour. The suspension was filtered, the precipitate was washed with portions of methylene chloride and the filtrate was diluted to a volume of 16 liters with methylene chloride. This solution was then washed with 3×8.0 liters (total of 24 liters) of 10% (w/v) phosphate buffer, pH 5.5. The methylene chloride solution was dried over 300 grams sodium sulfate and T.L.C. (System Two) indicated completion of the reaction. The solution was vacuum filtered and concentrated to a volume of 0.9 liter. The mixture was vacuum filtered and the solid was washed with 3×0.1 liter of methylene chloride. The volume of this solution was 1.2 liters.

This solution was stirred, 100.0 grams (0.243 moles) of Fmoc-β-(t-butyl)-L-Aspartic acid and 30.7 grams (0.243 moles) of diisopropylcarbodiimide were added. The mixture was stirred for 1 hour. T.L.C. (System One) indicated that the reaction was complete.

With the suspension being stirred, 441 mls (3.661 moles) of 4-aminomethylpiperidine was added and stirred for one hour. The suspension was vacuum filtered, the precipitate was washed with portions of methylene chloride and the filtrate was diluted to a volume of 16 liters with methylene chloride. This solution was washed with 3×8.0 liters (total of 24 liters) of 10% (w/v) phosphate buffer pH 5.5 The methylene chloride solution was dried over 300 grams of sodium sulfate and T.L.C. (System Two) indicated that the reaction was complete. The solution was vacuum filtered and concentrated to a volume of 0.9 liter. The mixture was vacuum filtered and the solid was washed with 3×0.1 liter of methylene chloride. The volume of this solution was 1.2 liters.

This solution was stirred, 93.2 grams (0.243 moles) of Fmoc-O-(T-butyl)-L-Serine and 30.7 grams (0.243 moles) of diisopropylcarbodiimide were added. The mixture was stirred for 1 hour and T.L.C. (System One) indicated the reaction was complete.

With the suspension being stirred, 441 mls (3.661 moles) of 4-aminomethylpiperidine was added and stirred for one hour. The suspension was vacuum filtered, the precipitate was washed with portions of methylene chloride and the filtrate was diluted to a volume of 16 liters with methylene chloride. This solution was washed with 3×8.0 liters (total of 24 liters) of 10% (w/v) phosphate buffer pH 5.5. The methylene chloride solution was dried over 300 grams of sodium sulfate and T.L.C. (System Two) indicated that the reaction was complete. The solution was vacuum filtered and concentrated to dryness.

The residue was dissolved in 0.3 liters of methylene chloride, vacuum filtered and solid was washed with 2×0.17 liter of methylene chloride.

The filtrate was stirred, 0.16 liter (1.695 moles) of acetic anhydride and 22.4 grams (0.221 moles) of triethylamine were added. The solution was stirred for 1 hour. T.L.C. (System Two) indicated the reaction was complete. The solution was concentrated to an oily residue. The residue was triturated with 3×0.5 liters of diisopropyl ether. The solid was vacuum filtered and the white solid was dried to yield 119.3 grams (0.157 moles) of a white solid.

An Erlenmeyer flask equipped with magnetic stirrer was charged with 17.9 grams (0.023 moles) of the white solid and 0,179 liters of a 95% (v/v) solution of trifluoroacetic acid in methylene chloride was added. The solution was stirred for two hours and H.P.L.C. (95/5 0.1% trifluoroacetic acid/acetonitrile isocratic at 220 nm, 1,0 ml/min., 5 microns, $C_{18}$ column) indicated that the reaction was complete.

The solution was concentrated and the residue was triturated with 2×0.1 liter of diisopropyl ether. The solid was vacuum filtered and dried to yield 10.46 grams of product (65% yield).

Figure 2:
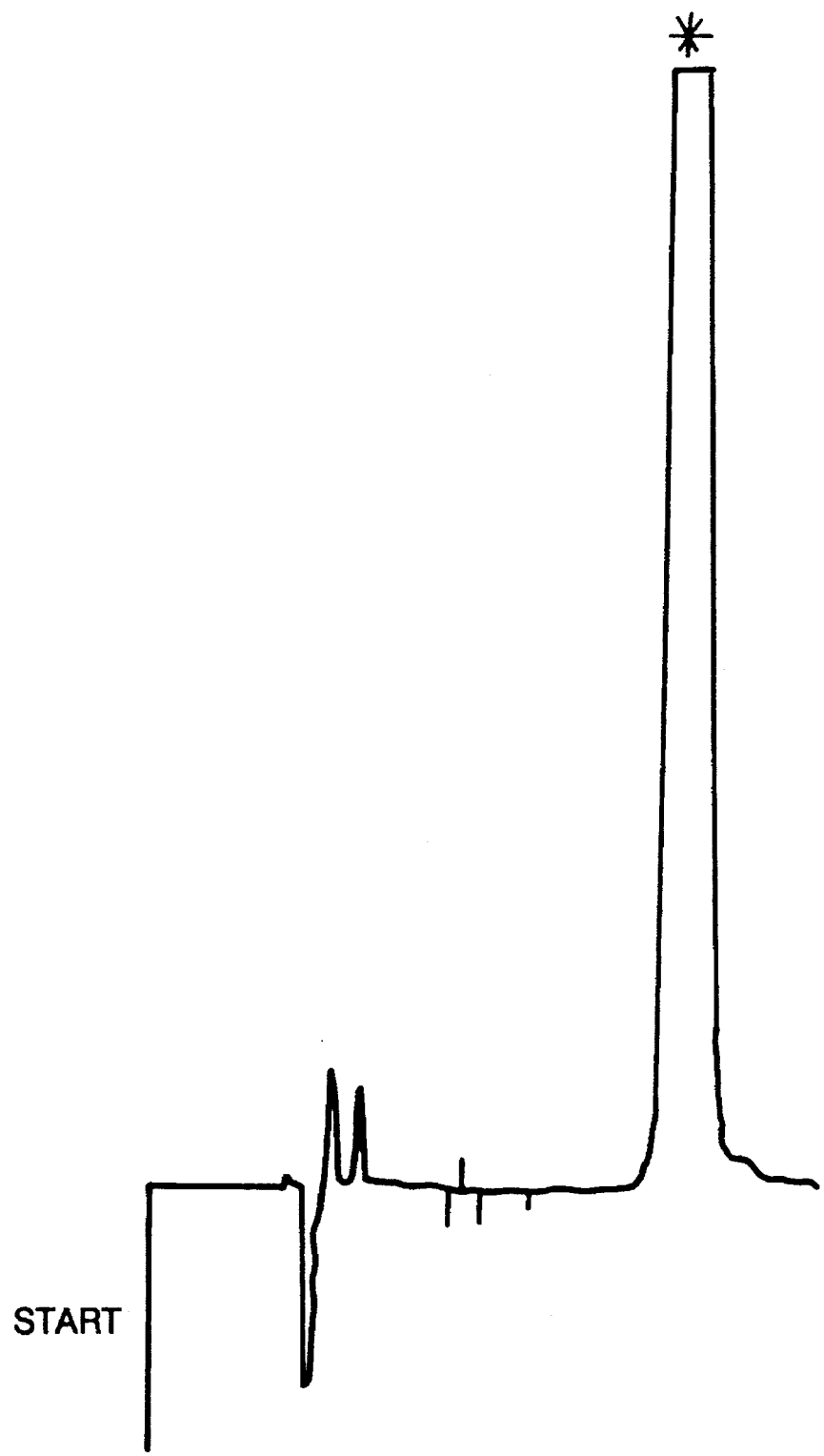
FIG. 2 is a high pressure liquid chromatograph of Acetyl-Ser-Asp-Lys-Pro-OH (SEQ ID NO:2) (purified product) prepared by the procedure shown in FIG. 1, illustrating absorbance at 220 nm versus time.

The crude product thus obtained was further purified by preparative H.P.L.C. The chromatogram of the purified product (with its corresponding peak denoted by an asterisk) is shown in FIG. 2.

EXAMPLE 2

Synthesis of H-Ser-Asp-Lys-Pro-OH (SEQ ID NO:1)

A 250 ml Erlenmeyer flask, equipped with magnetic stir bar, was charged with 1.44 grams (0.0069 moles) of L-Proline t-butyl ester hydrochloride, 3.56 grams (0.0076 moles) of Fmoc-(ε-Boc-L-Lysine) and 37.6 mls of methylene chloride. The suspension was stirred and 0.96 grams (0.0076 moles) of diisopropylcarbodiimide and 0.70 grams (0.0069 moles) of triethylamine were added. The mixture was stirred for 1 hour. T.L.C. (System One) indicated that the reaction was complete.

With the suspension being stirred, 13.8 mls (0.1146 moles) of 4-aminomethylpiperidine were added and stirred for one hour. The suspension was filtered, the precipitate was washed with portions of methylene chloride, and the filtrate was diluted to a volume of 500 mls with methylene chloride. This solution was washed with 3×250 mls (total of 750 mls) of 10% (w/v) phosphate buffer (pH 5.5). The methylene chloride solution was dried over 9.4 grams sodium sulfate and T.L.C. (System Two) indicated that the reaction was complete. The solution was vacuum filtered and concentrated to an oily residue. The residue was dissolved in 18.8 mls of methylene chloride, vacuum filtered and the solid was washed with 3×6.3 mls of methylene chloride. The volume of this solution was 37.6 mls.

This solution was stirred, 3.13 grams (0.0076 moles) of Fmoc-β-(t-butyl)-L-Aspartic acid and 0.960 grams (0.0076 moles) of diisopropylcarbodiimide were added. The mixture was stirred for 1 hour and T.L.C. (System One) indicated that the reaction was complete.

The suspension was stirred, 13.8 mls (0.1146 moles) of 4-aminomethylpiperidine were added and stirred for one hour. The suspension was vacuum filtered, the precipitate was washed with portions of methylene chloride, and the filtrate was diluted to a volume of 500 mls with methylene chloride. This solution was washed with 3×250 mls (total of 750 mls) of 10% (w/v) phosphate buffer (pH 5.5). The methylene chloride solution was dried over 9.4 grams sodium sulfate and T.L.C. (System Two) indicated that the reaction was complete. The solution was vacuum filtered, divided into halves and one half was concentrated to an oily residue. (The remaining half of the solution was used in another experiment.) The residue was dissolved in 9.4 mls of methylene chloride, vacuum filtered and the solid was washed with 3×3.13 mls of methylene chloride. The volume of this solution was 18.8 mls.

This solution was stirred, 1.46 grams (0.0038 moles) of Fmoc-O-(t-butyl)-L-Serine and 0.48 grams (0.0038 moles) of diisopropylcarbodiimide were added. The mixture was stirred for 1 hour and T.L.C. (System One) indicated that the reaction was complete.

The suspension was stirred, 6.9 mls (0.0573 moles) of 4-aminomethylpiperidine were added and stirred for one hour. The suspension was vacuum filtered, the precipitate was washed with portions of methylene chloride, and the filtrate was diluted to a volume of 250 mls with methylene chloride. This solution was washed with 3×125 mls (total of 375 mls) of 10% (w/v) phosphate buffer (pH 5.5). The methylene chloride solution was dried over 4.7 grams sodium sulfate and T.L.C. (System Two) indicated that the reaction was complete. The solution was vacuum filtered and concentrated to an oily residue.

The oil was dissolved in 1 ml methylene chloride, 17.8 mls (0.231 moles) of trifluoroacetic acid were added, and mixture was stirred for two hours.

Figure 3:
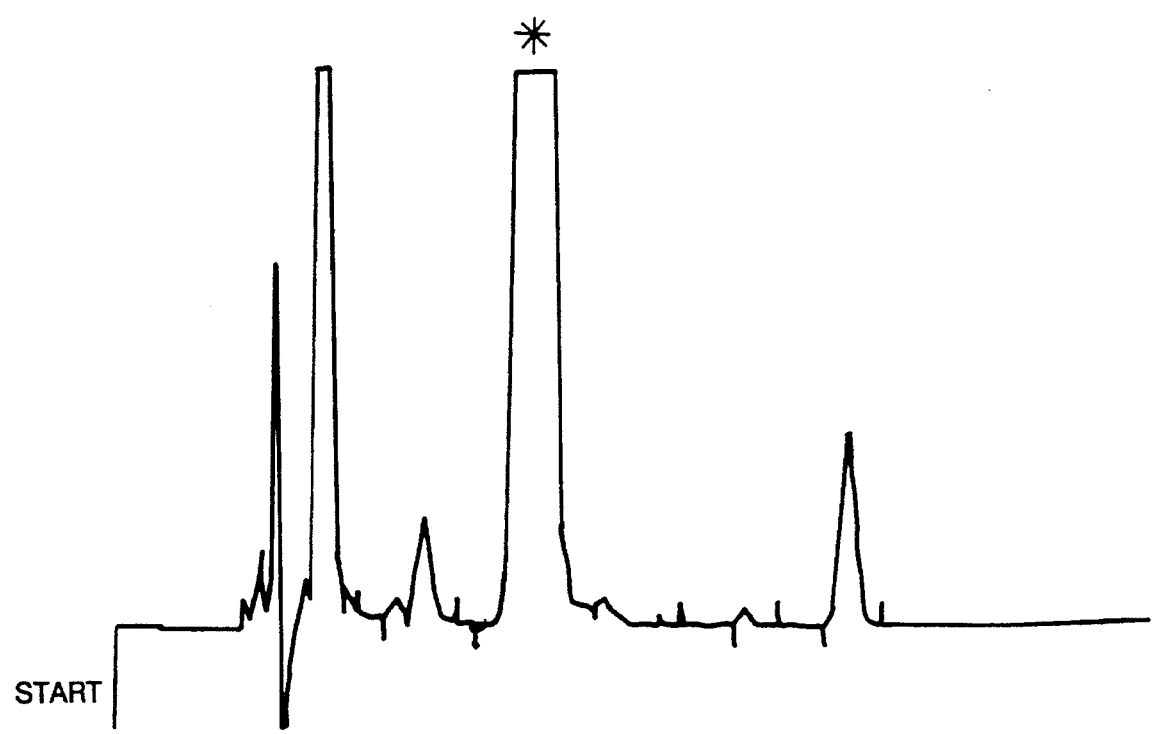
FIG. 3 is a high pressure liquid chromatograph of H-Ser-Asp-Lys-Pro-OH (SEQ ID NO:1) (crude product) prepared by a procedure similar to that shown in FIG. 1, illustrating absorbance at 220 nm versus time.

The solution was concentrated to an oil. The oil was triturated twice with 10 mls of diisopropyl ether, and the solid was dried. The solid was suspended in 10 mls of deionized water, 15 mls of aqueous 1 N acetic acid was added and the solution was lyophilized to yield 1.52 grams of a crude product. A sample of the crude product was taken for H.P.L.C. (95/5 0.1% trifluoroacetic acid/acetonitrile isocratic at 220 nm 1.0 ml/min, 5 micron $C_{18}$ column). The result is shown in FIG. 3 with the peak corresponding to the peptide product denoted by an asterisk.

The overall yield of the crude product was estimated to be 82%. The crude product was further purified by preparative H.P.L.C., the final yield being 53%.

The preceding examples can be repeated with success by substituting the generically or specifically described reactants and/or operating conditions of this invention for those used in these examples. For instance, any peptide or its acyl derivative containing 2–10 amino acids can be prepared in a similar manner by consecutively coupling proper amino acids, followed by acylation with a proper acylating agent, if necessary. When Cys is a building block of the peptide or its acyl derivative to be synthesized, an base-stable protecting group, such as triphenylmethyl, can be employed.

Also note that the reactants used in the present synthetic method are either commercially available or can be readily prepared following procedures well known in the art of peptide synthesis.

From the foregoing description, one skilled in the art can easily ascertain the essential characteristics of this invention, and without departing from the spirit and scope thereof, can make various changes and modifications of the invention to adapt it to various usages and conditions. Thus, other embodiments are also within the claims.

What is claimed is:

1. A continuous liquid phase synthetic method for preparing a peptide containing 3–10 amino acid residues with or without modification at the C-terminus or an N-acyl derivative thereof, which method comprises the steps of:

(a) coupling a first amino acid or a derivative thereof to a second amino acid via an amide bond in an organic solvent containing a substituted carbodiimide, with said first amino acid or derivative thereof having both its non-side chain carboxyl functionality and its side-chain functionalities, if any and necessary, blocked by base-stable groups and said second amino acid with its non-side chain amino functionality blocked by Fmoc and its side chain functionalities, if any and necessary, blocked by base-stable groups;

(b) detaching said Fmoc with ammonia, a primary amine, or a secondary amine;

(c) coupling an additional amino acid to the Fmoc-detached coupled product via an amide bond in an organic solvent containing a substituted carbodiimide, with said additional amino acid having its non-side chain amino functionality blocked by Fmoc and its side chain functionalities, if any and necessary, blocked by base-stable groups;

(d) detaching said Fmoc with ammonia, a primary amine, or a secondary amine;

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:1:

Ser Asp Lys Pro
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: Xaa is Serine whose amino
            functionality is substituted with an acetyl group.

( x i ) SEQUENCE DESCRIPTION: SEQ ID NO:2:

Xaa Asp Lys Pro
    1

(e) repeating steps (c) and (d) until the length of said peptide or said N-acyl derivative is achieved;

(f) acylating the non-side chain amino group of the Fmoc-detached coupled product from the previous step; and (g) detaching said base-stable groups;

wherein said first amino acid or derivative thereof corresponds to a first residue which is the C-terminal residue in said peptide or said N-acyl derivative, said second amino acid corresponds to a second residue adjacent to the first residue in said peptide or said N-acyl derivative, and said additional amino acid corresponds to a third residue adjacent to said second residue in said peptide or said N-acyl derivative; providing that when said peptide, rather than said N-acyl derivative, is to be synthesized, step (f) is omitted.

2. The synthetic method of claim 1, wherein said organic solvent is methylene chloride, chloroform, or dichloroethane.

3. The synthetic method of claim 2, wherein said organic solvent is methylene chloride.

4. The synthetic method of claim 1, wherein said substituted carbodiimide is diisopropylcarbodiimide, dicyclohexylcarbodiimide, or N-ethyl-N'-(3-dimethylaminopropyl)carbodiimide.

5. The synthetic method of claim 4, wherein said substituted carbodiimide is diisopropylcarbodiimide.

6. The synthetic method of claim 1, wherein said Fmoc is detached with 4-aminomethylpiperidine, piperidine, or tris (2-aminoethyl) amine.

7. The synthetic method of claim 6, wherein said Fmoc is detached with 4-aminomethylpiperidine.

8. The synthetic method of claim 1, wherein said detached Fmoc is removed by filtration and subsequent washing with an acidic aqueous solution.

9. The synthetic method of claim 8, wherein said acidic aqueous solution is a phosphate buffer.

10. The synthetic method of claim 8, wherein said organic solvent is methylene chloride and said Fmoc is detached with 4-aminomethylpiperidine.

11. The synthetic method of claim 1, wherein said base-stable groups are detached with trifluoroacetic acid.

12. The synthetic method of claim 10, wherein said base-stable groups are detached with trifluoroacetic acid.

13. The synthetic method of claim 1, wherein said N-acyl derivative is to be synthesized and a strong base is added in step (f).

14. The synthetic method of claim 13, wherein said strong base is triethylamine or diisopropylethylamine.

15. The synthetic method of claim 1, wherein said peptide or said N-acyl derivative contains 3–7 amino acid residues.

16. The synthetic method of claim 15, wherein said peptide or said N-acyl derivative contains 4 amino acid residues.

17. The synthetic method of claim 16, wherein said peptide or said N-acyl derivative is an N-acetyl derivative.

18. The synthetic method of claim 16, wherein said peptide or said N-acyl derivative is H-Ser-Asp-Lys-Pro-OH (SEQ ID NO:1) or Acetyl-Ser-Asp-Lys-Pro-OH (SEQ ID NO:2).

19. The synthetic method of claim 18, wherein said base-stable protecting groups for Ser, Asp, Lys and Pro are t-butyl, t-butyl, t-butyloxycarbonyl, and t-butyl, respectively.

20. The synthetic method of claim 18, wherein said organic solvent is methylene chloride, chloroform, or dichloroethane.

21. The synthetic method of claim 20, wherein said organic solvent is methylene chloride.

22. The synthetic method of claim 18, wherein said substituted carbodiimide is diisopropylcarbodiimide, dicyclohexylcarbodiimide, or N-ethyl-N'-(3-dimethylaminopropyl)carbodiimide.

23. The synthetic method of claim 22, wherein said substituted carbodiimide is diisopropylcarbodiimide.

24. The synthetic method of claim 18, wherein said Fmoc is detached with 4-aminomethylpiperidine, piperidine, or tris (2-aminoethyl) amine.

25. The synthetic method of claim 24, wherein said Fmoc is detached with 4-aminomethylpiperidine.

26. The synthetic method of claim 18, wherein said detached Fmoc is removed by filtration and subsequent washing with an acidic aqueous solution.

27. The synthetic method of claim 26, wherein said acidic aqueous solution is a phosphate buffer.

28. The synthetic method of claim 26, wherein said organic solvent is methylene chloride and said Fmoc is detached with 4-aminomethylpiperidine.

29. The synthetic method of claim 18, wherein said base-stable groups are detached with trifluoroacetic acid.

30. The synthetic method of claim 18, wherein Acetyl-Ser-Asp-Lys-Pro-OH (SEQ ID NO:2)is to be synthesized and a strong base is added in step (f).

31. The synthetic method of claim 30, wherein said strong base is triethylamine or diisopropylethylamine.

32. A continuous liquid phase synthetic method for preparing a peptide containing 2–10 amino acid residues with or without modification at the C-terminus or an N-acyl derivative thereof, which method comprises the steps of:

(a) coupling a first amino acid or a derivative thereof to a second amino acid via an amide bond in an organic solvent containing a substituted carbodiimide, with said first amino acid or derivative thereof having both its non-side chain carboxyl functionality and its side-chain functionalities, if any and necessary, blocked by base-stable groups and said second amino acid with its non-side chain amino functionality blocked by Fmoc and its side chain functionalities, if any and necessary, blocked by base-stable groups;

(b) detaching said Fmoc with ammonia, a primary amine, or a secondary amine;

(c) coupling an additional amino acid to the Fmoc-detached coupled product via an amide bond in an organic solvent containing a substituted carbodiimide, with said additional amino acid having its non-side chain amino functionality blocked by Fmoc and its side chain functionalities, if any and necessary, blocked by base-stable groups;

(d) detaching said Fmoc with ammonia, a primary amine, or a secondary amine;

(e) repeating steps (c) and (d) until the length of said peptide or said N-acyl derivative is achieved;

(f) acylating the non-side chain amino group of the Fmoc-detached coupled product from the previous step; and (g) detaching said base-stable groups;

wherein said first amino acid or derivative thereof corresponds to a first residue which is the C-terminal residue in said peptide or said N-acyl derivative, said second amino acid corresponds to a second residue adjacent to the first residue in said peptide or said N-acyl derivative, and said additional amino acid corresponds to a third residue adjacent to said second residue in said peptide or said N-acyl derivative; providing that when said peptide or said N-acyl derivative contains two amino acid residues, steps (c) through (e) are omitted; and further providing that when said peptide, rather than said N-acyl derivative, is to be synthesized, step (f) is omitted; and further providing said detached Fmoc is removed by filtration and subsequent washing with an acidic aqueous solution.

33. The synthetic method of claim 32, wherein said acidic aqueous solution is a phosphate buffer.

34. The synthetic method of claim 32, wherein said organic solvent is methylene chloride and said Fmoc is detached with 4-amino methylpiperidine.

35. The synthetic method of claim 34, wherein said base-stable groups are detached with trifluoroacetic acid.

36. The synthetic method of claim 32, wherein said peptide or said acyl derivative is H-Ser-Asp-Lys-Pro-OH (SEQ ID NO:1) or Acetyl-Ser-Asp-Lys-Pro-OH (SEQ ID NO:2).

37. The synthetic method of claim 36, wherein said acidic aqueous solution is a phosphate buffer.

38. The synthetic method of claim 36, wherein said organic solvent is methylene chloride and said Fmoc is detached with 4-amino methylpiperidine.

* * * * *